Figure 1A:
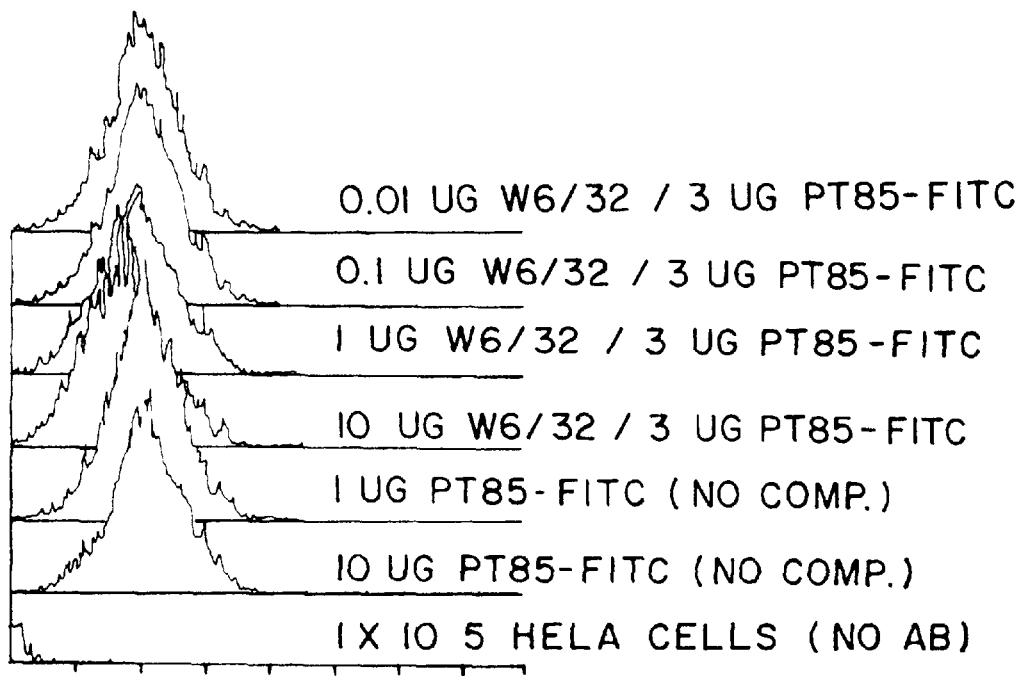

United States Patent [19]
Chappel

[11] Patent Number: 6,096,537
[45] Date of Patent: *Aug. 1, 2000

[54] CELLS WITH MULTIPLE ALTERED EPITOPES ON A SURFACE ANTIGEN FOR USE IN TRANSPLANTATION

[75] Inventor: Scott C. Chappel, Milton, Mass.

[73] Assignee: Diacrin, Inc., Charlestown, Mass.

[*] Notice: This patent is subject to a terminal disclaimer.

[21] Appl. No.: 08/946,637

[22] Filed: Oct. 7, 1997

Related U.S. Application Data

[63] Continuation of application No. 08/240,150, May 10, 1994, Pat. No. 5,679,340, which is a continuation-in-part of application No. 08/220,741, Mar. 31, 1994, abandoned.

[51] Int. Cl.[7] .............................. C12N 5/00; A61F 13/00; G01N 33/53; C07K 16/00

[52] U.S. Cl. ..................... 435/325; 424/422; 424/133.1; 424/143.1; 424/93.7; 435/7.1; 435/7.2; 435/7.21; 530/388.22

[58] Field of Search ................... 424/93.7, 422, 424/133.1, 143.1; 435/325, 7.1, 7.2, 7.21; 530/388.22

[56] References Cited

U.S. PATENT DOCUMENTS

| | | | |
|---|---|---|---|
| 4,009,257 | 2/1977 | Thomas et al. | 424/85 |
| 4,399,123 | 8/1983 | Oliver et al. | 424/95 |
| 5,283,058 | 2/1994 | Faustman | 424/88 |
| 5,679,340 | 10/1997 | Chappel | 424/93.1 |

FOREIGN PATENT DOCUMENTS

| | | |
|---|---|---|
| 0 314 863 | 5/1989 | European Pat. Off. . |
| WO 92/04033 | 3/1992 | WIPO . |
| WO 92/09688 | 6/1992 | WIPO . |

OTHER PUBLICATIONS

Barnstable, C.J. et al. (1978) "Production of Monoclonal Antibodies to Group A Erythrocytes, HLA and Other Human Cell Surface Antigens—New Tools for Genetic Analysis" *Cell* 14: 9–20.

Cooper, D.K.C. (1992) "Is Xenotransplantation a Realistic Clinical Option?" *Transplantation Proceedings* 24(6): 2393–2396.

Doetschman, T. et al. (1987) "Targetted correction of a mutant HPRT gene in mouse embryonic stem cells" *Nature* 330: 576–578.

Faustman, D. and C. Coe (1991) "Prevention of Xenograft Rejection by Masking Donor HLA Class I Antigens" *Science* 252: 1700–1702.

Faustman, D. and C. Coe (1992) "Xenograft Acceptance by Masking Donor Antigens" *Transplantation Proceedings* 24(6): 2854–2855.

(List continued on next page.)

*Primary Examiner*—Hankyel Park
*Attorney, Agent, or Firm*—Lahive & Cockfield, LLP; Amy E. Mandragouras, Esq.; Megan E. Williams

[57] ABSTRACT

Cells suitable for transplantation which have at least two different epitopes on a surface antigen altered prior to transplantation to inhibit rejection of the cells following transplantation into an allogeneic or xenogeneic recipient are disclosed. These cells are more successfully transplanted than cells which have only a single epitope on the surface antigen altered. Preferably, the antigen on the cell surface which is altered is an MHC class I antigen. Two different epitopes on an MHC class I antigen can be altered by contacting the cell with two molecules, such as antibodies or fragments thereof (e.g., F(ab')$_2$ fragments), which bind to two different epitopes on the antigen. Preferred epitopes on human MHC class I antigens to be altered are epitopes recognized by the monoclonal antibodies W6/32 and PT85. Improved methods for transplantation utilizing cells which have at least two different epitopes on a surface antigen altered prior to transplantation are also disclosed.

17 Claims, 3 Drawing Sheets

OTHER PUBLICATIONS

Faustman, D.L. et al. (1984) "Prevention of rejection of murine islet allografts by pretreatment with anti–dendritic cell antibody" Proceedings of the National Academy of Science, USA 81:3864–3868.

Gautam, A.M. et al. (1992), "Inhibition Of Experimental Autoimmune Encephalomyelitis By A Nonimmunogenic Non–Self Peptide That Binds To I–$A^U$1" *Journal of Immunology* 148(10): 3049–3054.

Goss, J.A. et al. (1993) "Specifiic Prolongation Of Allograft Survival By a T–Cell–Receptor–Derived Peptide" Proceedings of the National Academy of Sciences, USA 90(21): 9872–9876.

Hertel–Wulff, B. et al. (1994) "Long–Term Survival Of Pancreatic Islets In Diabetic Monkeys" *Cell Transplantation* 3(3): 216 (Abstract No. 20).

Hirata, A. and P.I. Terasaki (1972) "Masking of Human Transplantation Antigens by Diverse Substances"*Journal of Immunology* 108(6): 1542–1550.

Isobe, M. et al. (1992) "Specific Acceptance of Cardiac Allograft After Treatment with Antibodies to ICAM–1 and LFA–1" *Science* 255: 1125–1127.

Koller, B.H. and O. Smithies (1989) "Inactivating the $\beta_2$–microglobulin locus in mouse embryonic stem cells by homologous recombination" Proceedings of the National Academy of Science, USA 86:8932–8935.

Lacy, P.E. et al. (1979) "Prolongation of Islet Allograft Survival Following in vitro Culture (24° C.) and a Single Injection of ALS" *Science* 204:312–313.

Lafferty, K.J. et al. (1975) "Thyroid Allograft Immunogenicity is Reduced after a Period in Organ Culture" *Science* 188: 259–261.

Li, X. and D. Faustman (1993) "Use of Donor $\beta_2$–microglobulin–deficient Transgenic Mouse Liver Cells for Isografts, Allografts, and Xenografts" *Transplantation* 55(4): 940–946.

Lie, W.–R. et al. (1988) "Preparation and characterization of murine monoclonal antibodies to swine lymphocyte antigens" *Immunology* 64: 599–605.

Mackie, J.T. et al. (1989) "Monoclonal Antibodies to Bovine Major Histocompatability System Antigens" *Expl. Clin. Immunogenet.* 6: 179–184.

Munn, S.R. and C. Marjoribanks (1992) "Abrogation of Islet Immunogenicity Using an Anti–MHC Class I Monoclonal Antibody" Transplantation Proceedings 24(3): 1038–1039.

Munn, S.R. and C. Marjoribanks (1992) "Masking Donor Major Histocompatability Complex Class I Antigen on Allogenic Islets" Transplantation Proceedings 24(6): 2857.

Santoso, S. et al. (1986) "Receptor Patching and Capping of Platelet Membranes Induced by Monoclonal Antibodies" *Blood* 67(2): 343–349.

Soon–Shiong, P. et al. (1993) "Long–term reversal of diabetes by the injection of immunoprotected islets" Proceedings of the National Academy of Science, USA 90: 5843–5847.

Steele, D. et al. (1994) "Transplantation Of Pancreatic Islets in Diabetic Nonhuman Primates" Transplantation Proceedings 26(6): 3317–3318.

Stock, P.G. et al. (1989) "Modulation of MHC Class I Antigen Decreases Pancreatic Islet Immunogenicity" *Journal of Surgical Research* 46: 317–321.

Taylor, R.B. et al. (1971) "Redistribution and Pinocytosis of Lymphocyte Surface Immunoglobulin Molecules Induced by Anti–Immunoglobulin Antibody" *Nature New Biology* 233: 225–229.

Winearls, C.G. et al. (1979) "A Quantitative Comparison of Whole Antibody and F(ab')$_2$ in Kidney Allograft Enhancement" *Transplantation* 28: 36–39.

Zeng, Y. et al. (1994), "Inhibition Of Transplant Rejection By Pretreatment of Xenogeneic Pancreatic Islet Cells With Anti–ICAM–1 Antibodies" *Transplantation* 58(6): 681–689.

Zijlstra, M. et al. (1990) "$\beta$ 2–Microglobulin deficient mice lack CD4$^-$8$^+$ cytolytic T cells" *Nature* 344: 742–746.

- 0.01 UG W6/32 / 3 UG PT85-FITC
- 0.1 UG W6/32 / 3 UG PT85-FITC
- 1 UG W6/32 / 3 UG PT85-FITC
- 10 UG W6/32 / 3 UG PT85-FITC
- 1 UG PT85-FITC (NO COMP.)
- 10 UG PT85-FITC (NO COMP.)
- 1 X 10 5 HELA CELLS (NO AB)

- 0.01 UG W6/32 / 1 UG PT85-FITC
- 0.1 UG W6/32 / 1 UG PT85-FITC
- 1 UG W6/32 / 1 UG PT85-FITC
- 10 UG W6/32 / 1 UG PT85-FITC
- 1 UG PT85-FITC (NO COMP.)
- 10 UG PT85-FITC (NO COMP.)
- 1 X 10 5 HELA CELLS (NO AB)

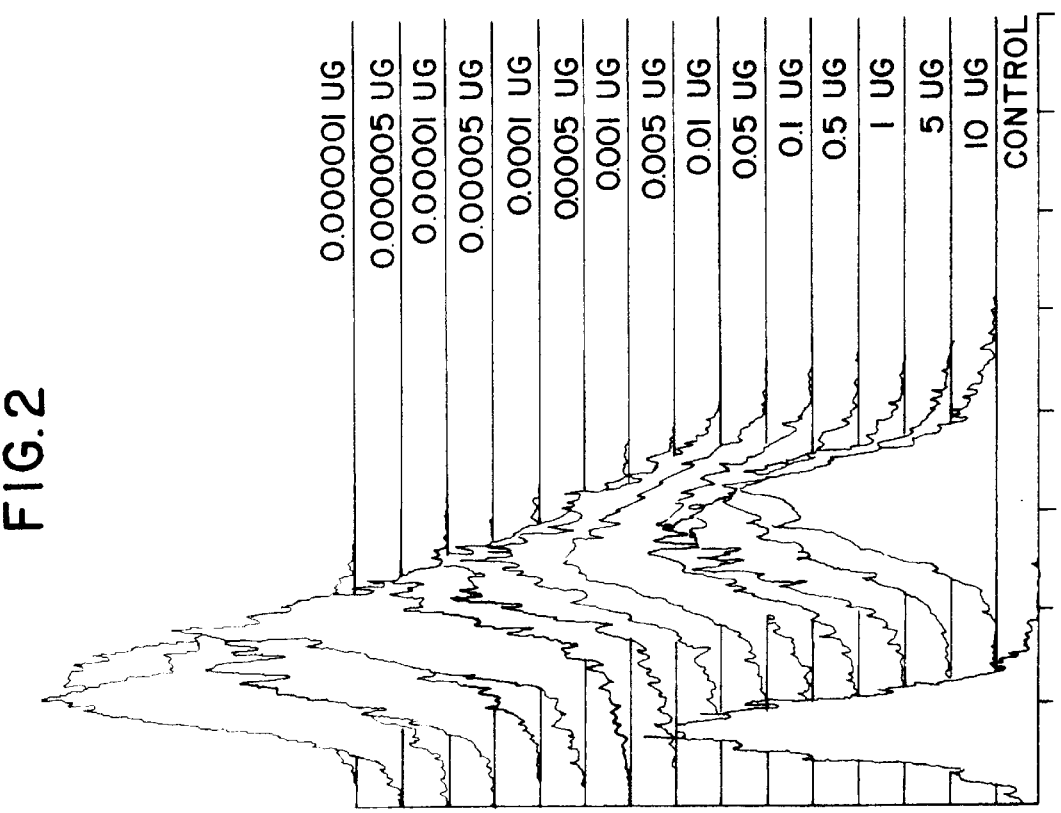

CELLS WITH MULTIPLE ALTERED EPITOPES ON A SURFACE ANTIGEN FOR USE IN TRANSPLANTATION

RELATED APPLICATION

This application is a continuation application of U.S. Ser. No. 08/240,150, filed May 10, 1994, now U.S. Pat. No. 5,679,340, which in turn is a continuation-in-part of U.S. application Ser. No. 08/220,741, filed Mar. 31, 1994, now abandoned. The contents of all the aforementioned application(s) are hereby incorporated by reference.

BACKGROUND OF THE INVENTION

A number of diseases are treated by the transplantation of tissue donated by other humans (allografts) or obtained from animals (xenografts). For example, insulin-dependent diabetes is often treated by transplantation of insulin-secreting pancreatic islet cells. While the transplanted cells may have the capacity to perform the desired function (e.g., secretion of insulin in response to rising levels of glucose), the graft typically fails as a result of immunological rejection. Shortly after transplantation, cells of the immune system of the recipient recognize the allogeneic or xenogeneic cells as foreign and proceed to attack the graft through both humoral and cellular routes. Allogeneic or xenogeneic cells are initially recognized by the recipient's immune system through antigenic determinants expressed on the surface of the cells. The predominant antigens recognized as "non-self" are major histocompatibility complex class I and class II antigens (MHC class I and class II). MHC class I antigens are expressed on virtually all parenchymal cells (e.g., pancreatic islet cells). In contrast, MHC class II antigens are expressed on a limited number of cell types, primarily B cells, macrophages, dendritic cells, Langerhans cells and thymic epithelium. The interaction of foreign MHC antigens with the T cell receptor on host T cells causes these cells to become activated. Following activation, the T cells proliferate and induce effector functions which result in cell lysis and destruction of the transplanted cells.

For transplantation to be a viable therapeutic option, approaches are needed to inhibit rejection of transplanted cells by the immune system of the recipient. One method for inhibiting this rejection process is by administration of drugs that suppress the function of the immune system. While drugs such as cyclophosphamide and cyclosporin effectively inhibit the actions of the immune system and thus allow graft acceptance, their use can cause generalized, non-specific immunosuppression in the graft recipient which leaves the recipient susceptible to other disorders such as infection and tumor growth. Additionally, administration of immunsuppressive drugs is often accompanied by other serious side effects such as renal failure and hypertension.

It has been shown that it is possible to alter an antigen on the surface of a cell prior to transplantation to "mask" the antigen from normal recognition by cells of the recipient's immune system (see Faustman and Coe (1991) Science 252:1700–1702 and WO 92/04033). For example, MHC class I antigens on transplanted cells can be altered by contacting the cells with a molecule which binds to the antigen, such as an antibody or fragment thereof (e.g., a F(ab')2 fragment) prior to transplantation. This alteration of MHC class I antigens modifies the interaction between the antigens on the cells and T lymphocytes in the recipient following transplantation to thereby inhibit rejection of the transplanted cells. Additional methods for reducing the immunogenicity of an allograft or xenograft to inhibit rejection of the graft following transplantation in a host are needed.

SUMMARY OF THE INVENTION

This invention features cells suitable for transplantation which have been treated prior to transplantation to reduce the immunogenicity of the cells and thereby inhibit rejection of the cells following transplantation into an allogeneic or xenogeneic recipient. Cells for use in transplantation have at least one antigen on the cell surface which is stimulates an immune response against the cell in an allogeneic or xenogeneic recipient. According to the invention, the cells are treated prior to transplantation to alter at least two different epitopes on the cell surface antigen. Alteration of the epitopes on the antigen results in a modification of an interaction between the antigen and a hematopoietic cell (e.g., a T lymphocyte) in the recipient, thereby inhibiting rejection of the transplanted cells. This invention is based, at least in part, on the discovery that alteration of two different epitopes on the same cell surface antigen on a cell suitable for transplantation is more effective in inhibiting rejection of the cell following transplantation than alteration of a single epitope on the antigen. This result is unexpected since it had been previously demonstrated that alteration of a single epitope on a cell surface antigen was sufficient to inhibit rejection of the cell by a recipient.

In a preferred embodiment, the antigen on the cell surface which is altered is an MHC class I antigen. Thus, two or more different epitopes on the same MHC class I antigen on a cell are altered prior to transplantation of the cell in an allogeneic or xenogeneic recipient. Alteration of two or more epitopes on the MHC class I antigen occurs by contacting the cell in vitro with two or more molecules which bind to the epitopes. Preferably, the molecule which binds to an epitope is an antibody, or fragment or derivative thereof, which binds to the epitope but does not activate complement or induce lysis of the cell. A preferred antibody fragment is an F(ab')$_2$ fragment.

Epitopes on human MHC class I antigens to be altered according to the invention include epitopes which are recognized by a monoclonal antibody W6/32 and a monoclonal antibody PT85. Thus, a preferred combination of molecules which can be used to alter two different epitopes on the same human MHC class I antigen are fragments of the W6/32 and PT85 monoclonal antibodies, such as F(ab')$_2$ fragments.

Accordingly, this invention provides improved methods for reducing the immunogenicity of a cell suitable for transplantation into an allogeneic or xenogeneic recipient in which two or more epitopes of an antigen on the cell surface which stimulates an immune response against the cell in the recipient are altered. The cells and methods of the invention can greatly improve the effectiveness of allogeneic or xenogeneic graft transplantation, with fewer side effects than immunosuppressive drugs such cyclosporin.

BRIEF DESCRIPTION OF THE DRAWINGS

FIG. 1 is a flow cytometric profile depicting the binding of increasing concentrations of FITC-labeled PT85 $F(ab')_2$ fragments to HeLa cells.

FIG. 2 is a flow cytometric profile depicting the binding of FITC-labeled PT85 $F(ab')_2$ fragments to HeLa cells in the presence of increasing amounts of unlabeled W6/32 $F(ab')_2$ fragments or PT85 $F(ab')_2$ fragments.

DETAILED DESCRIPTION OF THE INVENTION

This invention pertains to improved cells and methods for transplantation of such cells in allogeneic and xenogeneic recipients. The improvements provided by the invention involve alteration of at least two different epitopes on an antigen on the surface a cell prior to transplantation to inhibit rejection of the cell following transplantation into an allogeneic or xenogeneic recipient subject. Accordingly, the invention provides a cell suitable for transplantation which has at least two different epitopes on an antigen altered prior to transplantation to inhibit rejection of the cell following transplantation. Epitopes on an antigen on the surface of a donor cell are altered to modify an interaction between the antigen and a hematopoietic cell in a recipient. In an unaltered state, the antigen stimulates an immune response against the cell (also referred to herein as the donor cell) when the cell is administered to a heterologous subject (also referred to herein as the recipient or host). By altering epitopes on the antigen, the normal immunological recognition of the donor cell by the immune system cells of the recipient is modified. Immunological recognition of the altered form of epitopes on the antigen results in donor cell-specific long term unresponsiveness in the recipient.

Alteration of two or more epitopes on an antigen on a donor cell prior to administering the cell to a recipient interferes with the initial phase of recognition of the donor cell by cells of the host's immune system subsequent to administration of the cell. Interference with this initial phase of recognition of the donor cell may induce immunological nonresponsiveness or tolerance in the host, thereby preventing the induction of effector phases of an immune response (e.g., cytotoxic T cell generation, antibody production etc.) which are ultimately responsible for rejection of foreign cells in a normal immune response. As used herein, the term "altered" encompasses changes that are made to two or more epitopes on donor cell antigen which reduce the immunogenicity of the antigen to thereby interfere with immunological recognition of the antigen by the recipient's immune system. Preferably, immunological nonresponsiveness to the donor cells in the recipient subject is generated as a result of alteration of the antigen. The term altered is not intended to include complete elimination of the antigen on the donor cell since delivery of an inappropriate or insufficient signal to the host's immune cells (e.g., T lymphocytes) may be necessary to achieve immunological nonresponsiveness.

At least two different epitopes on an antigen on a donor cell are altered according to the invention to modify an interaction between the antigen and a hematopoietic cell in an allogeneic or xenogeneic recipient, thereby inhibiting a specific immune response against the donor cell in the recipient. The interaction between the antigen and the hematopoietic cell may be an indirect interaction (e.g., mediated by soluble factors which induce a response in the hematopoietic cell) or, more preferably, is a direct interaction (e.g., binding interaction) between the antigen and a molecule present on the surface of the hematopoietic cell. As used herein, the term hematopoietic cell is intended to include T lymphocytes, B lymphocytes, monocytes and other antigen presenting cells. Preferably, the two epitopes to be altered are present on an antigen which interacts with a T lymphocyte in the recipient (e.g., the antigen normally binds to a receptor on the surface of a T lymphocyte).

As used herein, the term "epitope" refers to a conformational or linear determinant on a cell surface structure, such as a cell surface protein. An epitope on a protein is a portion of the protein which is specifically recognized by a molecule, e.g., an antibody or a T cell receptor. Conformational epitopes are formed as a result of a three-dimensional folding of a protein whereas linear epitopes depend only on the primary amino acid sequence within the epitope. Typically, antibodies bind to conformational epitopes on an immunogenic protein and a single protein can have many different epitopes which can be bound by different antibodies.

In a preferred embodiment, the antigen on the donor cell to be altered is an MHC class I antigen. Thus, at least two different epitopes on the same MHC class I antigen on the donor cell are altered prior to transplantation. MHC class I antigens are present on almost all cell types. In a normal immune response, self MHC molecules function to present antigenic peptides to the T cell receptor (TCR) on the surface of self T lymphocytes. In immune recognition of allogeneic or xenogeneic cells, foreign MHC antigens (most likely together with a peptide bound thereto) on donor cells are recognized by the T cell receptor on host T cells to elicit an immune response. Epitopes on an MHC class I antigen on a donor cell are altered to interfere with recognition of the MHC class I antigen by T cells in an allogeneic or xenogeneic host (e.g., portions of the MHC class I antigen which are normally recognized by the T cell receptor are blocked or "masked" such that normal recognition of the MHC class I antigen can no longer occur). Additionally, an altered form of an MHC class I antigen which is exposed to host T cells (i.e., available for presentation to the host T cell receptor) may deliver an inappropriate or insufficient signal to the host T cell such that, rather than stimulating an immune response against the allogeneic or xenogeneic cell, donor cell-specific T cell non-responsiveness is induced. For example, it is known that T cells which receive an inappropriate or insufficient signal through their T cell receptor (e.g., by binding to an MHC antigen in the absence of a costimulatory signal, such as that provided by B7) become anergic rather than activated and can remain refractory to restimulation for long periods of time (see for example Damle et al. (1981) *Proc. Natl. Acad. Sci. USA* 78:5096–5100; Lesslauer et al. (1986) *Eur. J Immunol.* 16:1289–1295; Gimmi, et al. (1991) *Proc. Natl. Acad. Sci. USA* 88: 6575–6579; Linsley et al. (1991) *J Exp. Med.* 173:721–730; Koulova et al. (1991) *J Exp. Med.* 173:759–762; Razi-Wolf, et al. (1992) *Proc. Natl. Acad. Sci. USA* 89:4210–4214).

Alternative to MHC class I antigens, two or more epitopes on other surface antigens on donor cells can be altered. For example, epitopes on MHC class II antigens can be altered. Similar to MHC class I antigens, MHC class II antigens function to present antigenic peptides to the T cell receptor on T lymphocytes. However, MHC class II antigens are present on a limited number of cell types (primarily B cells, macrophages, dendritic cells, Langerhans cells and thymic epithelial cells). In addition to or alternative to MHC antigens, epitopes on other antigens on a donor cell which interact with molecules on host T cells and which are known to be involved in immunological rejection of allogeneic or xenogeneic cells can be altered. Other donor cell antigens known to interact with host T cells and to contribute to rejection of a donor cell include molecules which function to increase the avidity of the interaction between a donor cell and a host T cell. Due to this property, these molecules are typically referred to as adhesion molecules (although they may serve other functions in addition to increasing the adhesion between a donor cell and a host T cell). Examples of preferred adhesion molecules which can be altered according to the invention include LFA-3, ICAM-1 and ICAM-2. These molecules are ligands for the CD2 and LFA-1 receptors, respectively, on T cells. By altering an adhesion molecule on the donor cell, (such as LFA-3, ICAM-1 or similarly functioning molecule), the ability of the host's T cells to bind to and interact with the donor cell is reduced. Both LFA-3 and ICAM-1 are found on endothelial cells within blood vessels in transplanted organs such as kidney and heart. Altering these antigens may facilitate transplantation of any vascularized implant, by preventing recognition of those antigens by CD2+ and LFA-1+ host T-lymphocytes.

The presence of MHC molecules or adhesion molecules such as LFA-3, ICAM-1 etc. on a particular donor cell can be assessed by standard procedures known in the art. For example, the donor cell can be reacted with a labeled antibody directed against the molecule to be detected (e.g., MHC molecule, ICAM-1, LFA-1 etc.) and the association of the labeled antibody with the cell can be measured by a suitable technique (e.g., immunohistochemistry, flow cytometry etc.).

A preferred method for altering at least two different epitopes on an antigen on a donor cell to inhibit an immune response against the cell is to contact the cell with at least two different molecules which bind to the epitopes. It is preferred that the cell be contacted with at least two different molecules which bind to the different epitopes prior to administering the cell to a recipient (i.e., the cell is contacted with the molecule in vitro). For example, the cell can be incubated with the molecules which bind to the epitopes under conditions which allow binding of the molecules to the epitopes and then any unbound molecules can be removed (such as described in the Exemplification to follow). Following administration of the donor cell to a recipient, the molecules remain bound to the epitopes on the surface antigen for a sufficient time to interfere with immunological recognition by host cells and induce non-responsiveness in the recipient.

Preferably, the molecule for altering an epitope on a donor cell is an antibody, or fragment or derivative thereof which retains the ability to bind to the epitope. For use in therapeutic applications, it is necessary that an antibody which binds the epitopes to be altered be unable to fix complement, thus preventing donor cell lysis. Antibody complement fixation can be prevented by deletion of an Fc portion of an antibody, by using an antibody isotype which is not capable of fixing complement, or, less preferably, by using a complement fixing antibody in conjunction with a drug which inhibits complement fixation. Alternatively, amino acid residues within the Fc region of an antibody which are important for activating complement (see e.g., Tan et al. (1990) *Proc. Natl. Acad. Sci. USA* 87:162–166; Duncan and Winter (1988) Nature 332: 738–740) can be mutated to reduce or eliminate the complement-activating ability of an intact antibody. Likewise, amino acids residues within the Fc region of an antibody which are necessary for binding of the Fc region to Fc receptors (see e.g. Canfield, S. M. and S. L. Morrison (1991) *J Exp. Med.* 173:1483–1491; and Lund, J. et al. (1991) *J Immunol.* 147:2657–2662) can also be mutated to reduce or eliminate Fc receptor binding if an intact antibody is to be used.

A preferred antibody fragment for altering an epitope is a F(ab')$_2$ fragment. Antibodies can be fragmented using conventional techniques. For example, the Fc portion of an antibody can be removed by treating an intact antibody with pepsin, thereby generating a F(ab')$_2$ fragment. In a standard procedure for generating F(ab')$_2$ fragments, intact antibodies are incubated with immobilized pepsin and the digested antibody mixture is applied to an immobilized protein A column. The free Fc portion binds to the column while the F(ab')$_2$ fragments passes through the column. The F(ab')$_2$ fragments can be further purified by HPLC or FPLC. F(ab')$_2$ fragments can be treated to reduce disulfide bridges to produce Fab' fragments.

An antibody, or fragment or derivative thereof, to be used to alter multiple epitopes on an antigen can be derived from polyclonal antisera containing antibodies reactive with a number of epitopes on the antigen. More preferably, however, two different epitopes on the same antigen are altered using two different monoclonal antibodies which bind to two different epitopes on the same antigen (e.g., an MHC class I antigen). Polyclonal and monoclonal antibodies which bind to different epitopes on one or more antigens can be prepared by standard techniques known in the art. For example, a mammal, (e.g., a mouse, hamster, or rabbit) can be immunized with an antigen (e.g., an MHC class I antigen) or with a cell which expresses the antigen (e.g., on the cell surface) to elicit an antibody response against the antigen in the mammal. Alternatively, tissue or a whole organ which expresses the antigen can be used to elicit antibodies. The progress of immunization can be monitored by detection of antibody titers in plasma or serum. Standard ELISA or other immunoassay can be used with the antigen to assess the levels of antibodies. Following immunization, antisera can be obtained and, if desired, polyclonal antibodies isolated from the sera. To produce monoclonal antibodies, antibody producing cells (lymphocytes) can be harvested from an immunized animal and fused with myeloma cells by standard somatic cell fusion procedures thus immortalizing these cells and yielding hybridoma cells. Such techniques are well known in the art. For example, the hybridoma technique originally developed by Kohler and Milstein ((1975) *Nature* 256:495–497) as well as other techniques such as the human B-cell hybridoma technique (Kozbar et al., (1983) *Immunol. Today* 4:72), and the EBV-hybridoma technique to produce human monoclonal antibodies (Cole et al. (1985) *Monoclonal Antibodies in Cancer Therapy*, Allen R. Bliss, Inc., pages 77–96) can be used. Hybridoma cells can be screened immunochemically for production of antibodies specifically reactive with the antigen and monoclonal antibodies isolated.

Another method of generating specific antibodies, or antibody fragments, reactive against epitopes on an antigen is to screen expression libraries encoding immunoglobulin genes, or portions thereof, expressed in bacteria with the antigen (or a portion thereof). For example, complete Fab fragments, $V_H$ regions, $F_V$ regions and single chain antibodies can be expressed in bacteria using phage expression libraries. See for example Ward et al., (1989) *Nature* 341:544–546; Huse et al., (1989) *Science* 246:1275–1281; and McCafferty et al. (1990) *Nature* 348:552–554. Alternatively, the SCID-hu mouse can be used to produce antibodies, or fragments thereof (available from Genpharm). Antibodies of the appropriate binding specificity which are made by these techniques can be used to alter an antigen on a donor cell.

An antibody, or fragment thereof, produced in a non-human subject can be recognized to varying degrees as foreign when the antibody is administered to a human subject (e.g., when a donor cell with an antibody bound thereto is administered to a human subject) and an immune response against the antibody may be generated in the subject. One approach for minimizing or eliminating this problem is to produce chimeric or humanized antibody derivatives, i.e., antibody molecules comprising portions which are derived from non-human antibodies and portions which are derived from human antibodies. Chimeric antibody molecules can include, for example, the antigen binding domain from an antibody of a mouse, rat, or other species, with human constant regions. A variety of approaches for making chimeric antibodies have been described. See, for example, Morrison et al., *Proc. Natl. Acad. Sci. U.S.A.* 81, 6851 (1985); Takeda et al., *Nature* 314, 452 (1985), Cabilly et al., U.S. Pat. No. 4,816,567; Boss et al., U.S. Pat. No. 4,816,397; Tanaguchi et al., European Patent Publication EP171496; European Patent Publication 0173494, United Kingdom Patent GB 2177096B. For use in therapeutic applications, it is preferred that an antibody used to used to alter different epitopes on an antigen not contain an Fc portion. Thus, a humanized F(ab')$_2$ fragment in which parts of the variable region of the antibody, especially the conserved framework regions of the antigen-binding domain, are of human origin and only the hypervariable regions are of non-human origin is a preferred antibody derivative. Such altered immunoglobulin molecules can be produced by any of several techniques known in the art, (e.g., Teng et al., *Proc. Natl. Acad. Sci. U.S.A.*, 80, 7308–7312 (1983); Kozbor et al., *Immunology Today*, 4, 7279 (1983); Olsson et al., *Meth. Enzymol.*, 92, 3–16 (1982)), and are preferably produced according to the teachings of PCT Publication W092/06193 or EP 0239400. Humanized antibodies can be commercially produced by, for example, Scotgen Limited, 2 Holly Road, Twickenham, Middlesex, Great Britain.

The ability of two different monoclonal antibodies which bind to the same antigen to bind to different epitopes on the antigen can be determined using a competition binding assay as described in the Exemplification. Briefly, one monoclonal antibody is labeled and used to stain cells which express the antigen. The ability of the unlabeled second monoclonal antibody to inhibit the binding of the first labeled monoclonal antibody to the antigen on the cells is then assessed. If the second monoclonal antibody binds to a different epitope on the antigen than does the first antibody, the second antibody will be unable to competitively inhibit the binding of the first antibody to the antigen.

Each of the cell surface antigens having two or more epitopes to be altered, e.g., the MHC class I antigens, MHC class II antigens, LFA-3 and ICAM-1 is well-characterized and antibodies reactive with these antigens are commercially available. For example, an antibody reactive with human MHC class I antigens (i.e., an anti-HLA class I antibody), W6/32, is available from the American Tissue Culture Society (ATCC HB 95). This antibody was raised against human tonsillar lymphocyte membranes and binds to HLA-A, HLA-B and HLA-C (Barnstable, C. J. et al. (1978) Cell 14:9–20). Another anti-MHC class I antibody which can be used is PT85 (see Davis, W. C. et al. (1984) *Hybridoma Technology in Agricultural and Vetrinary Research.* N. J. Stern and H. R. Gamble, eds., Rownman and Allenheld Publishers, Totowa, N.J., p121; commercially available from Veterinary Medicine Research Development, Pullman Wash.). This antibody was raised against swine leukocyte antigens (SLA) and binds to class I antigens from several different species (e.g., pig, human, mouse, goat). An anti-ICAM-1 antibody can be obtained from AMAC, Inc., Maine. Hybridoma cells producing anti-LFA-3 can be obtained from the American Type Culture Collection, Rockville, Ma.

As demonstrated in the Exemplification, the combined use of $F(ab')_2$ fragments of the monoclonal antibodies W6/32 and PT85 to alter two different epitopes on MHC class I antigens on human pancreatic islet cells is more effective in inhibiting rejection of the islet cells when transplanted than is the use of either W6/32 or PT85 alone. W6/32 and PT85 can be demonstrated to recognize different epitopes on human MHC class I antigens by a competitive binding assay, wherein increasing amounts of unlabeled W6/32 are unable to inhibit the binding of labeled PT85 to human cells (see the Exemplification and FIG. 2). Accordingly, preferred epitopes to be altered on human MHC class I antigens are the epitopes which are recognized by the monoclonal antibodies W6/32 and PT85. These epitopes can be altered by using W6/32 and PT85 in combination (e.g., W6/32 and PT85 $F(ab')_2$ fragments, as described in the Exemplification) or by using other monoclonal antibodies which recognize the same epitopes as W6/32 and PT85. A monoclonal antibody which recognizes the same epitope as either W6/32 or PT85 can be prepared by standard techniques for producing monoclonal antibodies (described herein) and then identified based upon the ability of the monoclonal antibody to competitively inhibit the binding of either W6/32 or PT85 to human cells (e.g., a monoclonal antibody which recognizes the same epitope as PT85 will competitively inhibit the binding of PT85 to human cells).

Two or more suitable antibodies, or fragments or derivatives thereof, for use in the invention can be identified based upon their ability to inhibit an immunological rejection of allogeneic or xenogeneic cells using a protocol such as that described in the Exemplification. Briefly, the antibodies (or antibody fragments) are incubated for a short period of time (e.g., 30 minutes at room temperature) with cells or tissue to be transplanted, any unbound antibody is washed away. The cells or tissue are then transplanted into a recipient animal. The ability of the multiple antibody pretreament to inhibit or prevent rejection of the transplanted cells or tissue is then determined by monitoring the function of the graft and/or by monitoring for signs of rejection of the cells or tissue compared to untreated controls.

Other molecules which bind to an epitope on an antigen on a donor cell and produce a functionally similar result as antibodies, or fragments or derivatives thereof, (e.g., other molecules which interfere with the interaction of the antigen with a hematopoietic cell and induce immunological nonresponsiveness) can be used to alter the epitope on the donor cell. One such molecule is a soluble form of a ligand for an antigen (e.g., a receptor) on the donor cell which could be used to alter an epitope on the antigen on the donor cell. For example, a soluble form of CD2 (i.e., comprising the extracellular domain of CD2 without the transmembrane or cytoplasmic domain) can be used to alter an epitope on LFA-3 on the donor cell by binding to LFA-3 on donor cells in a manner analogous to an antibody. Alternatively, a soluble form of LFA-1 can be used to alter an epitope on ICAM-1 on the donor cell. A soluble form of a ligand can be made by standard recombinant DNA procedures, using a recombinant expression vector containing DNA encoding the ligand encompassing only the extracellular domain (i.e., lacking DNA encoding the transmembrane and cytoplasmic domains). The recombinant expression vector encoding the extracellular domain of the ligand can be introduced into host cells to produce a soluble ligand, which can then be isolated. Soluble ligands of use have a binding affinity for the receptor on the donor cell sufficient to remain bound to the receptor to interfere with immunological recognition and induce non-responsiveness when the cell is administered to a recipient (e.g., preferably, the affinity for binding of the soluble ligand to the receptor is at least about $10^{-7}$ M). Additionally, the soluble ligand can be in the form of a fusion protein comprising the receptor binding portion of the ligand fused to another protein or portion of a protein. For example, an immunoglobulin fusion protein which includes an extracellular domain, or functional portion of CD2 or LFA-1 linked to an immunoglobulin heavy chain constant region (e.g., the hinge, CH2 and CH3 regions of a human immunoglobulin such as IgGl) can be used. Immunoglobulin fusion proteins can be prepared, for example, according to the teachings of Capon, D. J. et al. (1989) *Nature* 337:525–531 and U.S. Pat. No. 5,116,964 to Capon and Lasky.

Another type of molecule which can be used to alter an MHC antigen (e.g., and MHC class I antigen) is a peptide which binds to the MHC antigen and interferes with the interaction of the MHC antigen with a T lymphocyte. In one embodiment, the soluble peptide mimics a region of the T cell receptor which contacts the MHC antigen. This peptide can be used to interfere with the interaction of the intact T cell receptor (on a T lymphocyte) with the MHC antigen. Such a peptide binds to a region of the MHC molecule which is specifically recognized by a portion of the T cell receptor (e.g., the alpha-I or alpha-2 loop of an MHC class I antigen), thereby altering the MHC class I antigen and inhibiting recognition of the antigen by the T cell receptor. In another embodiment, the soluble peptide mimics a region of a T cell surface molecule which contacts the MHC antigen, such as a region of the CD8 molecule which contacts an MHC class I antigen or a region of a CD4 molecule which contacts an MHC class II antigen. For example, a peptide which binds to a region of the alpha-3 loop of an MHC class I antigen can be used to inhibit binding to CD8 to the antigen, thereby inhibiting recognition of the antigen by T cells. T cell receptor-derived peptides have been used to inhibit MHC class I-restricted immune responses (see e.g., Clayberger, C. et al. (1993) Transplant Proc. 25:477–478) and prolong allogeneic skin graft survival in vivo when injected subcutaneously into the recipient (see e.g., Goss, J. A. et al. (1993) *Proc. Natl. Acad. Sci. USA* 90:9872–9876).

It is preferred that an antibody, or fragment or derivative thereof, which is used to alter an epitope have an affinity for binding to its target epitope of at least $10^{-7}$ M). The affinity of an antibody or other molecule for binding to an epitope on an antigen can be determined by conventional techniques (see Masan, D. W. and Williams, A. F. (1980) *Biochem. J* 187:1–10). Briefly, the antibody to be tested is labeled with $I^{125}$ and incubated with cells expressing the antigen at increasing concentrations until equilibrium is reached. Data are plotted graphically as [bound antibody]/[free antibody] versus [bound antibody] and the slope of the line is equal to the kD (Scatchard analysis).

The same or different types of molecules can be used to alter two or more different epitopes on a donor cell. In a preferred embodiment, two different antibodies (or fragments thereof) are used to alter two different epitopes. Alernatively, one epitope can be altered with one type of molecule and a second epitope can be altered with another type of molecule. For example, two different epitopes on the same MHC class I antigen can be altered using an anti-MHC class I antibody and an MHC-binding peptide.

Alternative to binding one or more molecules (e.g., an antibodies) to epitopes on an antigen on a donor cell to inhibit immunological rejection of the cell, the epitopes can be altered by other means. For example, epitopes can be directly altered (e.g., mutated) such that they can no longer interact normally with a hematopoietic cell (e.g., a T lymphocyte) in an allogeneic or xenogeneic recipient and induces immunological non-responsiveness to the donor cell in the recipient. For example, an altered form of an MHC class I antigen or adhesion molecule (e.g., LFA-3 or ICAM-1), in which two or more epitopes are mutated, can be created by mutagenesis and selected in in vitro culture based upon the failure of the molecule to contribute to T cell activation. An altered from of an MHC class I antigen or adhesion molecule delivers an inappropriate or insufficient signal to a T cell upon binding to a receptor on the T cell. A nucleic acid encoding the mutated form of the antigen (i.e., the antigen with mutated epitopes) can then be inserted into the genome of a non-human animal, either as a transgene or by homologous recombination (to replace the endogenous gene encoding the wild-type antigen). Cells from the non-human animal which express the mutated form of the antigen can then be used as a donor cell for transplantation into an allogeneic or xenogeneic recipient.

Accordingly, this invention provides an improved method for reducing the immunogenicity of a cell for transplantation into an allogeneic or xenogeneic cell recipient subject. Prior to transplantation cells are contacted with at least two different molecules which bind to at least two different epitopes on an antigen on the cell surface to alter the antigen to inhibit rejection of the cell when transplanted into a recipient subject. Such cells can then be administered to a subject. Preferably, the antigen which is altered is an MHC class I antigen and the molecules with which the cell is contacted are antibodies or fragments or derivatives thereof, such as $F(ab')_2$ fragments. For human cells, antibodies which bind to epitopes recognized by the monoclonal antibodies W6/32 and PT85 are preferred. This method is more effective for reducing the immunogenicity of a cell for transplantation than contacting the cell with a single molecule which binds to a single epitope on an antigen on the cell.

In the method of the invention for transplantation, the cell is administered to a subject (i.e., transplanted into the subject) after alteration of at least two different epitopes on an antigen on the surface of the donor cell. The term "subject" is intended to include mammals, preferably humans, in which an immune response is elicited against allogeneic or xenogeneic cells. A cell can be administered to a subject by any appropriate route which results in delivery of the cell to a desired location in the subject. For example, cells can be administered intravenously, subcutaneously, intramuscularly, intracerebrally, subcapsular (e.g., under the kidney capsule) or intraperitoneally. The cells can be administered in a physiologically compatible carrier, such as a buffered saline solution. When cells are within a tissue or organ, the tissue or organ can be transplanted into a suitable location in the subject by conventional techniques to administer the cells to the subject.

The methods of the invention can be applied to any type of cell which is suitable for transplantion (i.e, any type of cell which can be isolated or obtained in a form that can be transplanted to another subject). The cell can be a human cell or it can be a non-human cell. A preferred non-human cell is a porcine cell. Preferred cell types for use in the method of the invention are cells which can provide a therapeutic function in a disease or disorder. Examples of such cells include muscle cells (e.g., myoblasts, myocytes, myotubes), liver cells, pancreatic islet cells, neural cells and hematopoietic cells. For example, muscle cells can be transplanted into subjects suffering from a muscular dystrophy (e.g., Duchenne muscular dystrophy), pancreatic islet cells can be transplanted into a subject suffering from diabetes, neural cells can be transplanted into a subject suffering from Parkinson's disease or Huntington's disease, liver cells can be transplanted into a subject with hepatic cell dysfunction (e.g. in hypercholesterolemia, hemophilia or inherited emphysema), and hematopoietic cells can be transplanted into patients with hematopoietic or immunological dysfunction.

In addition to permitting transplantation of cells, the invention can facilitate transplantation of tissues or organs, e.g., kidney, heart, liver, lung, brain, and muscle tissue. Accordingly, the cells of the invention can be within a tissue or organ. When a cell is within a tissue, different epitopes on a surface antigen on the cells (e.g., an MHC class I antigen) can be altered by contacting the entire tissue with at least two different molecules (e.g., antibodies) which binds to different epitopes on the surface antigen (e.g., by incubating the tissue in a solution containing the molecules which binds the epitopes). Alternatively, when a cell is within an organ, epitopes on antigens on the surface of the cells (e.g., MHC class I antigens) can be altered by perfusing the organ with a solution containing at least two different molecules (e.g. antibodies) which bind to at least two different epitopes on cells of the organ. Organs are perfused with a solution containing the molecules using conventional techniques for organ perfusion.

While the invention has been described in particular with regard to altering two different epitopes on a donor cell, it will be appreciated that there may be yet further benefit in modifying additional epitopes on a donor cell. Accordingly, cells which have more than two epitopes altered (e.g., three, four, five etc. epitopes altered), and methods using these cells, are within the scope of this invention.

This invention is further illustrated by the following exemplification which should not be construed as limiting. The contents of all references and published patents and patent applications cited throughout the application are hereby incorporated by reference.

EXEMPLIFICATION

This example involves xenogeneic transplantation of MHC I positive human islet cells into non-immunosuppressed Balb/c mouse recipients.

Freshly isolated human islets were pretreated prior to transplantation with the following:

Group A: no treatment
Group B: masking of MHC I with F(ab')$_2$ W6/32
Group C: masking of MHC I with F(ab')$_2$ PT85
Group D: masking of MHC I with both W6/32 and PT85

Islet cells were isolated and purified according to standard methods, yielding clean human islet preparations, free of contaminating endothelial and fibroblast overgrowth.

Preparation of F(ab')2 Fragments

F(ab')$_2$ fragments of antibodies W6/32 and PT85 were generated using immobilized pepsin, as follows. Purified antibody was added, at 20 mg/ml in pH 4.7 digestion buffer and digested for 4.0 hours. The crude digest was removed from the pepsin and immediately neutralized with pH 7.0 binding buffer. The antibody mixture was applied to an immobilized Protein A column and the elute was collected for the F(ab')$_2$ fragments. Dialysis against phosphate buffered saline for 24 h using 50,000 molecular weight cut-off tubing was then performed to rid the digest of contaminating Fc fragments. CHAPS buffer was added to the dialysis bag at a concentration of 10 mM. The completeness of the digest and purification of the F(ab')$_2$ were monitored by silver staining of 15% SDS polyacrylamide gels. Final purification of the fragments was achieved by using a Superose 12 HPLC column. The completeness of Fc removal was demonstrated in an in vitro assay in which binding of the material to a target cell was followed with the addition of complement, and cytolysis of the pre-loaded target cells was measured by chromium release.

Figure 1B:
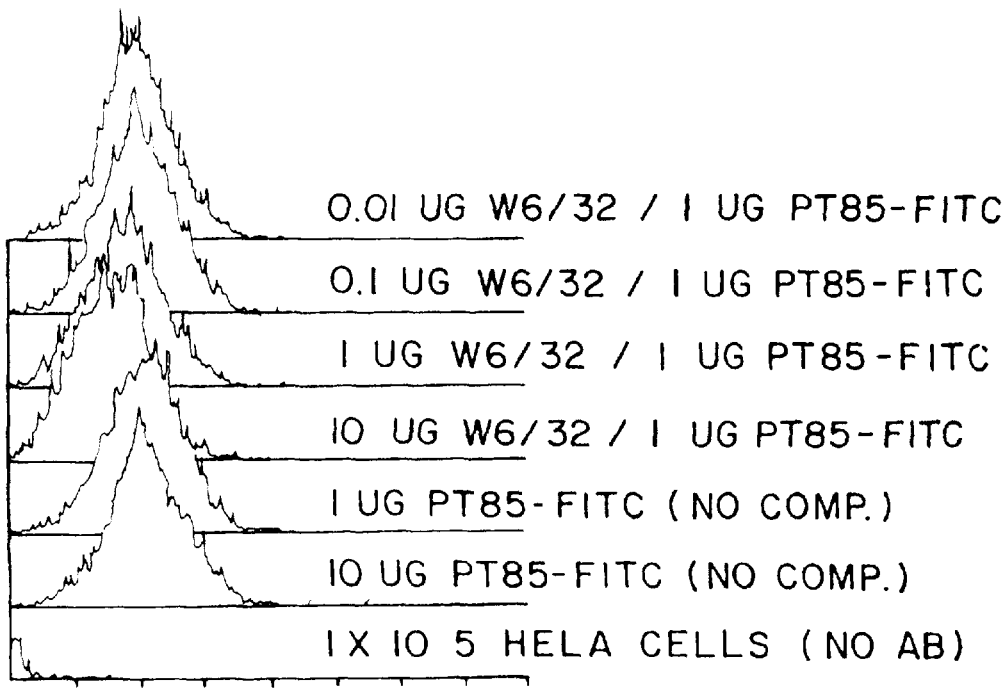
Figure 1C:
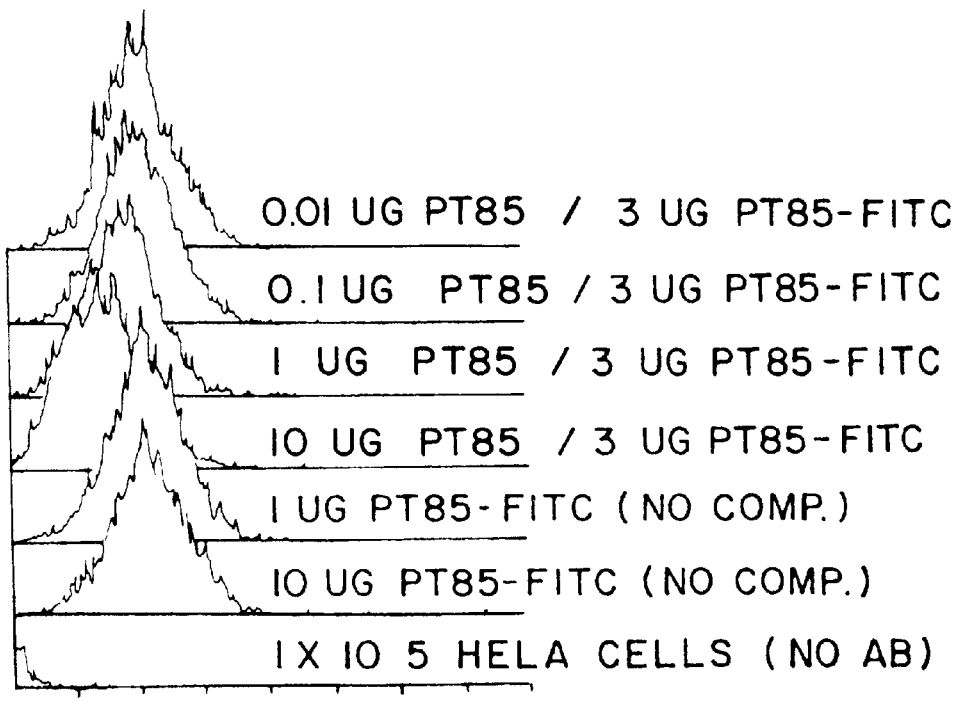
Figure 1D:
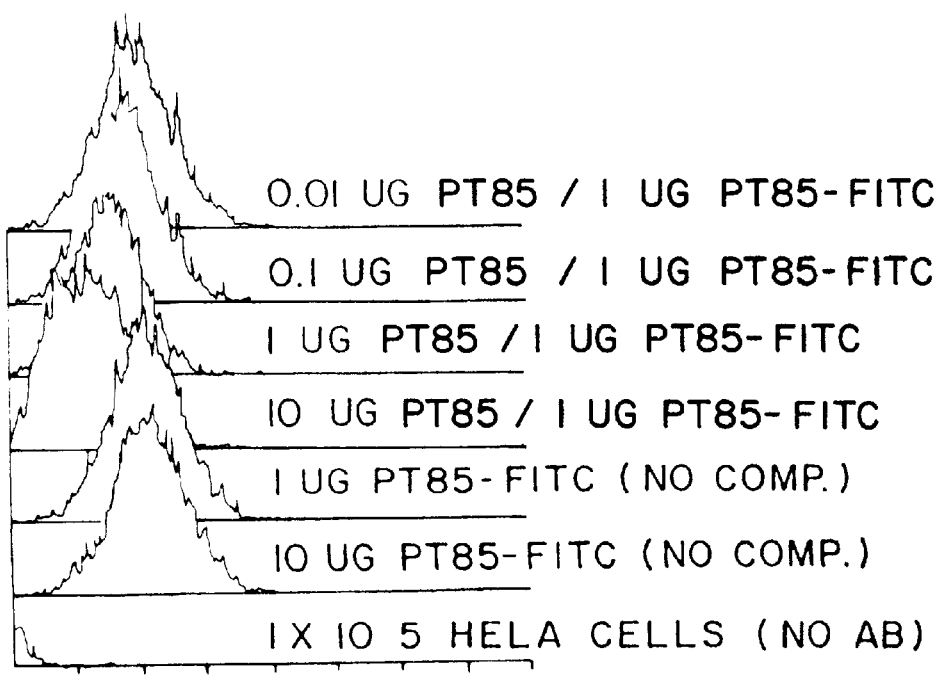

The binding of W6/32 and PT85 to different epitopes on MHC class I antigens was demonstrated in a binding competition assay. As a control, FITC-labeled PT85 F(ab')$_2$ fragments were used to stain HeLa cells, which were analyzed by flow cytometry. As shown in FIG. 1, increasing amounts of FITC-labeled PT85 F(ab')$_2$ fragments resulted in increasing amounts of surface staining of HeLa cells. Next, FITC-labeled PT85 F(ab')$_2$ fragments (either 3 μg or 1 μg) were used to stain HeLa cells in the presence of increasing amounts of unlabeled F(ab')$_2$ fragments, either unlabeled W6/32 or unlabeled PT85. As shown in FIG. 2, the top left panel depicts the binding of 3 μg of FITC-labeled PT85 in the presence of increasing amounts of unlabeled W6/32. Similarly, the top right panel depicts the binding of 1 μg of FITC-labeled PT85 in the presence of increasing amounts of unlabeled W6/32, whereas the bottom left panel depicts the binding of 3 μg of FITC-labeled PT85 in the presence of increasing amounts of unlabeled PT85. The bottom right panel of FIG. 2 depicts the binding of 1 μg of FITC-labeled PT85 in the presence of increasing amounts of unlabeled PT85. As shown in the flow cytometric profiles in FIG. 2, increasing amounts of unlabeled PT85 inhibit the binding of FITC-labeled PT85 F(ab')$_2$ fragments to HeLa cells, whereas increasing amounts of unlabeled W6/32 do not inhibit the binding of FITC-labeled PT85 F(ab')$_2$ fragments to HeLa cells. This demonstrates that W6/32 does not competitively inhibit binding of PT85 and therefore binds to a different epitope on MHC class I antigens than does PT85.

Masking of Pancreatic Islet Cells

F(ab')$_2$ fragments prepared as described above were incubated with human islet cells at a concentration of 1 μg of antibody per approximately 1 million cells for 30 min. at room temperature. After incubation, the treated or untreated islets were washed once with Hanks buffer containing 2% heat-inactivated fetal calf serum and then immediately transplanted under the kidney capsule of a mouse by syringe injection. The human islets were transplanted within four days of isolation. Sixteen animals (four per group) were transplanted with treated or untreated islets. At fourteen days post-injection, each animal was challenged with a glucose injection (30% wt/vol) following an overnight fast. A blood sample was obtained from each animal at 45–60 min. following injection and analyzed for human insulin in a radioimmunoassay employing an antibody that does not cross-react with mouse insulin.

Results of those determinations are shown below (Table 1):

TABLE 1

Plasma concentrations of human insulin in mice fourteen days after the injection of human islets under the kidney capsule

| Islet treatment | Plasma Insulin Conc at 14 days |
| --- | --- |
| None | 1.6 uU/ml |
| (Group A) | 2.2 |
|  | 2.3 |
|  | * |
| F(ab')$_2$ W6/32 | 1.7 |
| (Group B) | 1.6 |
|  | 1.7 |
|  | 1.7 |
| F (ab')$_2$ PT85 | 3.8 |
| (Group C) | 1.1 |
|  | 1.1 |
|  | * |
| Combination of W6/32 and PT85 | 3.5 |
| (Group D) | 3.8 |

TABLE 1-continued

Plasma concentrations of human insulin in mice fourteen days after the injection of human islets under the kidney capsule

| Islet treatment | Plasma Insulin Conc at 14 days |
|---|---|
| | 3.8 |
| | 3.8 |

*animal died before blood collection

The data of Table 1 demonstrate that treatment of human islets with one F(ab')₂ preparation alone was successful in allowing graft acceptance in only one of seven cases. Combining both of the antibodies allowed for graft acceptance in four of four animals.

Other Embodiments

Other embodiments are within the scope of the invention. For example, the procedures described above for treatment of islet cells can be used to treat other transplanted parenchymal cells such as liver cells. Like islet cells, liver cells express rejection-stimulating antigens, including MHC I antigens. Liver tissue can be obtained from brain dead donors or from non-human animals such as pigs. The cells can be dissociated by digestion with collagenase. Viable cells can be obtained and washed by centrifugation (at 700×g), elution, and resuspension. Epitopes on a surface antigen (e.g., MHC class I antigen) on the liver cells are altered by treatment with two or more different-specificity F(ab')₂ fragments as described above. Following alteration of the epitopes, cells are administered through the umbilical vein to the liver of the recipient patient.

In another embodiment, nerve cells obtained from a source (such as an abortus) are treated with a combination of different-specificity (F ab')₂ fragments and stereotaxically localized into the desired area of the brain, such as the corpus striatum. Dopaminergic or GABA-ergic neurons are used for the treatment of Parkinson's or Huntington's disease, respectively.

In another embodiment, muscle cells can be obtained from a donor (e.g., by biopsy of a living related donor or from a brain dead donor) using a 14–16 guage cutting trochar into a 1–2 inch skin incision. The fresh muscle plug can be lightly digested to a single cell suspension using collagenase, typsin and dispase at 37° C. Floating debris is removed with a pipet and media washes and the viable cell pellet is counted after centrifugation at 1000 rpm for 10 minutes. The cell count is then used to calculate the amount of antibody fragments to be used to alter epitopes on a surface antigen on the muscle cells. Muscle cells are treated with a combination of different-specificity (F ab')₂ fragments, as described above, and injected intramuscularly into a recipient patient in need of an increased store of muscle, e.g., an elderly patient with severe muscle wasting, or injected into a muscle group of a patient afflicted with Becker's or Duchenne muscular dystrophy.

In yet another embodiment, the cells which are altered according to the invention are genetically modified to express a gene product. The genetically modified cells can be transplanted into a recipient subject to deliver the gene product to the subject. Cells can be genetically modified to express a gene product by introducing nucleic acid encoding the gene product into the cell. For example, a cell can be infected with a recombinant virus (e.g., retrovirus, adenovirus) which contains the nucleic acid of interest. A non-human cell which is genetically modified to express a human gene product can be used to deliver the human gene product to a human subject by altering two or more epitopes on the surface of the non-human cell and transplanting the cell into the recipient subject. Techniques for producing genetically modified cells and their methods of use are described in detail in a related application entitled "*Genetically Modified Cells For Use In Transplantation*" filed on even date herewith (Attorney docket no. DNI-001). The contents of this application are incorporated herein by reference.

In yet another embodiment, a recipient subject into which altered cells of the invention are transplanted is also treated with a T cell inhibitory agent to further inhibit rejection of the transplanted cells. The T cell inhibitory agent inhibits T cell activity. For example, the T cell inhibitory agent can be an immunosuppressive drug. A preferred immunsuppressive drug is cyclosporin A. Other immunsuppressive drugs which can be used include FK506 and RS-61443. Such immunosuppressive drugs can be used in conjunction with a steroid (e.g., glucocorticoids such as prednisone, methylprednisolone and dexamethasone) or chemotherapeutic agents (e.g., azathioprine and cyclophosphamide), or both. Alternatively, the T cell inhibitory agent can be one or more antibodies which deplete T cell activity, such as antibodies directed against T cell surface molecules (e.g., anti-CD2, anti-CD3, anti-CD4 and/or anti-CD8 antibodies). Techniques for inhibiting rejection of transplanted cells combining alteration of a surface antigen(s) on the donor cells and treatment of the recipient with a T cell inhibitory agent are described in detail in a related application entitled "*Improved Methods for Transplantation Using Modified Cells and T Cell Inhibitory Agents*" filed on even date herewith (Attorney Docket No. DNI-002). The contents of this application are incorporated herein by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. A method for reducing the immunogenicity of a cell for transplantation having an antigen on its surface which stimulates an immune response against the cell in an allogeneic or xenogeneic recipient subject, comprising contacting the cell prior to transplantation with at least two different molecules which bind to at least two different epitopes on the antigen on the cell surface to alter the antigen such that rejection of the cell is inhibited upon transplantation into a recipient subject.

2. The method of claim 1, wherein the antigen on the cell surface is an MHC class I antigen.

3. The method of claim 2, wherein one of the molecules which binds to the different epitopes on the MHC class I antigen is an antibody, or fragment or derivative thereof, which binds to the antigen but does not activate complement or cause lysis of the cell.

4. The method of claim 3, wherein the antibody, or fragment or derivative thereof, is a F(ab')₂ fragment.

5. The method of claim 4, wherein the F(ab')₂ fragment binds to epitopes recognized by the monoclonal antibody W6/32 or PT85.

6. The method of claim 5, wherein the F(ab')₂ fragment is a F(ab')₂ fragment of monoclonal antibody W6/32 PT85.

7. The method of claim 2, wherein at least one molecule which binds to the epitopes is a peptide which binds to an MHC class I antigen.

8. The method of claim 1, wherein the cell is a pancreatic islet cell.

9. The method of claim 1, wherein the cell is a liver cell.

10. The method of claim 1, wherein the cell is a neural cell.

11. The method of claim 1, wherein the cell is a muscle cell.

12. The method of claim 1, wherein the cell is a hematopoietic cell.

13. The method of claim 1, wherein the cell is a human cell.

14. The method of claim 1, wherein the cell is a porcine cell.

15. The method of claim 1, wherein the molecule is a soluble form of a ligand on the surface of the donor cell.

16. The method of claim 15, wherein the molecule is a soluble form of CD2.

17. The method of claim 15, wherein the molecule is a soluble form of LFA-1.

* * * * *